(12) United States Patent
McCabe

(10) Patent No.: US 7,987,964 B2
(45) Date of Patent: Aug. 2, 2011

(54) ARTICLE TRANSFER AND PLACEMENT APPARATUS WITH ACTIVE PUCK

(75) Inventor: John A. McCabe, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 12/806,283

(22) Filed: Aug. 9, 2010

(65) Prior Publication Data

US 2010/0300838 A1 Dec. 2, 2010

Related U.S. Application Data

(63) Continuation of application No. 11/357,546, filed on Feb. 17, 2006, now Pat. No. 7,770,712.

(51) Int. Cl.
*B65G 13/02* (2006.01)
*B65G 15/42* (2006.01)
*B65G 17/46* (2006.01)
*B65G 37/00* (2006.01)
*B65G 47/82* (2006.01)

(52) U.S. Cl. ............... 198/471.1; 198/688.1; 198/689.1; 198/478.1; 198/598

(58) Field of Classification Search ............... 198/688.1, 198/689.1, 471.1, 478.1, 598
See application file for complete search history.

(56) References Cited

U.S. PATENT DOCUMENTS

| 4,608,115 | A * | 8/1986 | Schroth et al. | 156/519 |
| 5,660,665 | A * | 8/1997 | Jalonen | 156/163 |
| 7,398,870 | B2 * | 7/2008 | McCabe | 198/377.08 |

* cited by examiner

*Primary Examiner* — Gene Crawford
*Assistant Examiner* — Yolanda Cumbess
(74) *Attorney, Agent, or Firm* — Ryan Kromholz & Manion, S.C.

(57) ABSTRACT

An apparatus for transferring articles such as absorbent cores or disposable diaper chassis components from a rotary mechanism, such as a pad turner, to a linear mechanism, such as a conveyor, for further processing. A puck on the apparatus is capable of manipulating the article during this transfer procedure.

1 Claim, 7 Drawing Sheets

US 7,987,964 B2

ARTICLE TRANSFER AND PLACEMENT APPARATUS WITH ACTIVE PUCK

RELATED APPLICATION

This application is a continuation of U.S. patent application Ser. No. 11/357,546 filed 17 Feb. 2006 (now U.S. Pat. No. 7,770,712).

BACKGROUND OF THE INVENTION

This invention related to an apparatus for transferring articles such as absorbent pads in the manufacture of disposable absorbent articles such as diapers, incontinence control garments or female sanitary pads as they advance along a production line.

In the production and manufacture of disposable products such as sanitary napkins or pants-type diapers, it frequently becomes necessary to manufacture a component of the product in one orientation, and then to rotate that component part 90° so that it is suitably oriented for use in another step in the production process. Various devices have been developed for this purpose and are known to those experienced in the industry. Examples of such apparatus are those described in U.S. Pat. Nos. 4,726,876, 4,880,102, and 5,025,910, the disclosures of which are incorporated herein by reference.

As discussed above, a typical article to be reoriented by the apparatus of this invention is an absorbent pad. Because absorbent pads are typically comprised of several webs, an absorbent core and several elastic members, there is a tendency of these assemblies to contract and become distorted during transfer operations which greatly complicates handling of the pad during further processing. Control of the pad is important.

SUMMARY OF THE INVENTION

The apparatus of the present invention is an active puck that is capable of rotating and stretching an article between a pick-up and a lay-down point.

An active puck is disclosed that picks up an article from a first conveying means, the article traveling in a first orientation, carries, stretches and rotates the article, so the article is traveling in a second orientation, and deposits the article onto another conveying means. A cam plate comprising a guiding structure of increasing radius cooperates with a vacuum slide to urge stretching of the article is provided. A vacuum puck carries the article while the slide rotatably operates through the increasing (or decreasing) radius.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
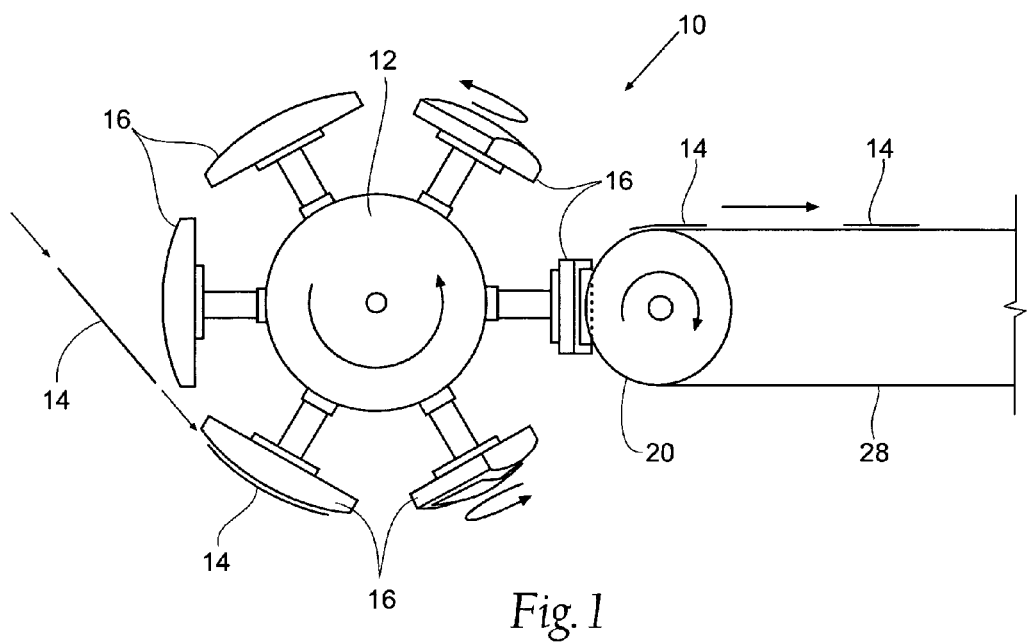
FIG. 1 is a fragmentary side elevation view, shown in diagrammatic form, of a pad transferring assembly.

Referring more particularly to the drawings, there is seen in FIG. 1 an apparatus 10 carrying pucks, or transfer heads 16, of the present invention. The apparatus 10 is adapted to receive a series of articles 14 from an upstream conveyor or vacuum drum (not shown) onto a pad turning device 12 which includes a plurality of radially extending transfer heads 16.

The location where articles 14 are received from the upstream point onto the pucks 16 is known as the pick up point. The location where articles 14 are deposited from the pucks 16 to a downstream drum or conveyor 20 is known as the lay down point.

The pad turning device 12 may be, for example, a rotary pad turner of the type more fully described in U.S. Pat. No. 5,025,910 which is incorporated herein by reference. The articles 14, such as absorbent pads, may be any elongated articles which need to be rotated approximately 90° during the course of a manufacturing operation. In the present invention, the elongated articles are also stretched away from their center point in a direction, such as a radial direction, away from the axis of the puck 16 as will be described later.

Such pad turning devices 12 are especially needed and are suited for use in connection with the manufacture and packaging of sanitary napkins as well as absorbent pads which are used in the assembly of disposable garments such as adult incontinence garments or children's training pants.

Also seen in FIG. 1, articles 14 are successively and individually picked-up by the transfer heads 16 of the pad transfer device 12. In the illustrated embodiment, the articles 14 are picked up from a vacuum drum (not shown). Various conventional conveying and direction changing devices such as rollers may be employed in the feeding of the web and do not form a part of this invention.

After the articles 14 have been rotated 90 degrees, they are deposited at the lay down point onto drum 20. The pucks 16 of the present invention can stretch the articles 14, as will be described below, and deposit them in the stretched condition onto drum 20. A conveyor 28 or the like transport the articles 14 for further processing or to a packaging device, as required by a particular application.

Figure 2:
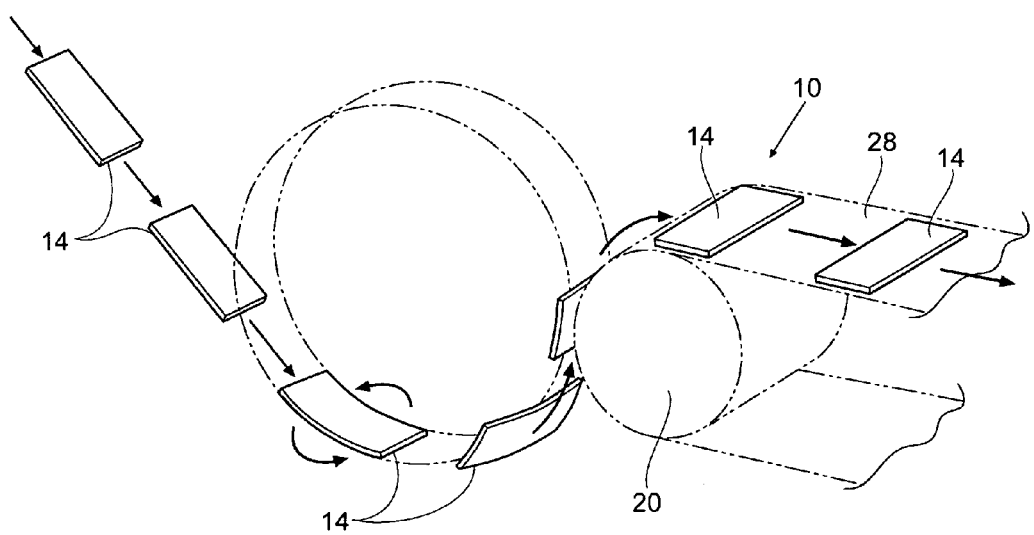
FIG. 2 is a perspective fragmentary, diagrammatic view, showing related apparatus by means of phantom lines and illustrating the path of movement of pads moving in accordance with the invention.

Referring to FIG. 2, there is seen a diagrammatic depiction of the travel path of the web 22 and the resultant pads 14 which are formed therefrom. In this depiction the various apparatus have been eliminated but are partially illustrated by means of phantom lines.

As can be seen, the article is rotated 90° from the pick up point to the lay down point, and is also stretched during this time it spends on the puck 16. The active puck 16 of this invention is more fully described in the remaining Figures.

Figure 3:
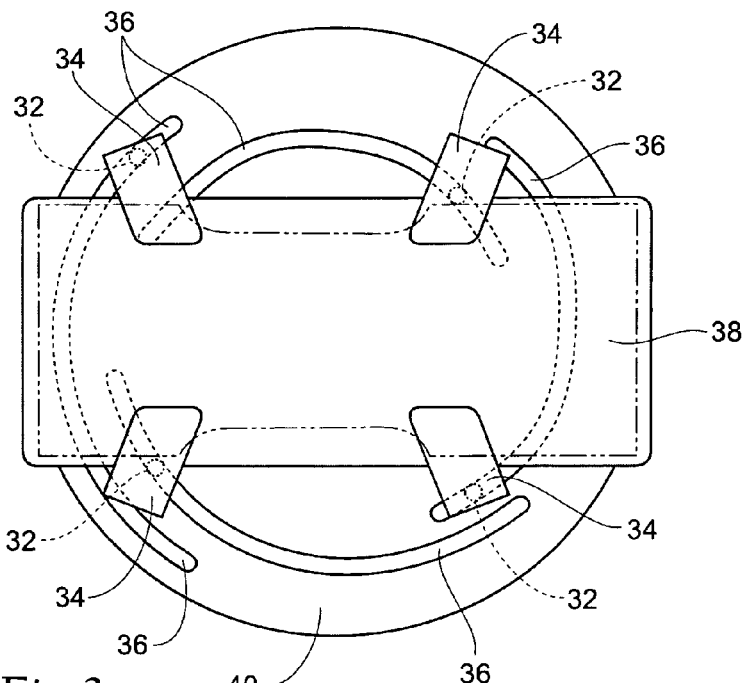
FIG. 3 is a top view of an embodiment of an active pad turning puck of the present invention.

As shown in FIG. 3, a top view of an embodiment of an active pad turning puck 16 of the present invention is shown. A plurality of vacuum slides 34 are positioned about a puck assembly 38. The vacuum slides 34 are intended to engage a portion of articles 14 (not shown) by vacuum ports 42, and manipulate by stretching or otherwise the articles 14. As is well known in the art, each of the segments can be connected internally to a source of vacuum. A pattern of holes is provided on the surface of each segment through which the internal vacuum acts to draw the pads 14 towards the surface. It is clear that this technology can be applied to the transfer and placement of many different types of articles in the disposable goods industry and other industries as well.

Figure 4:
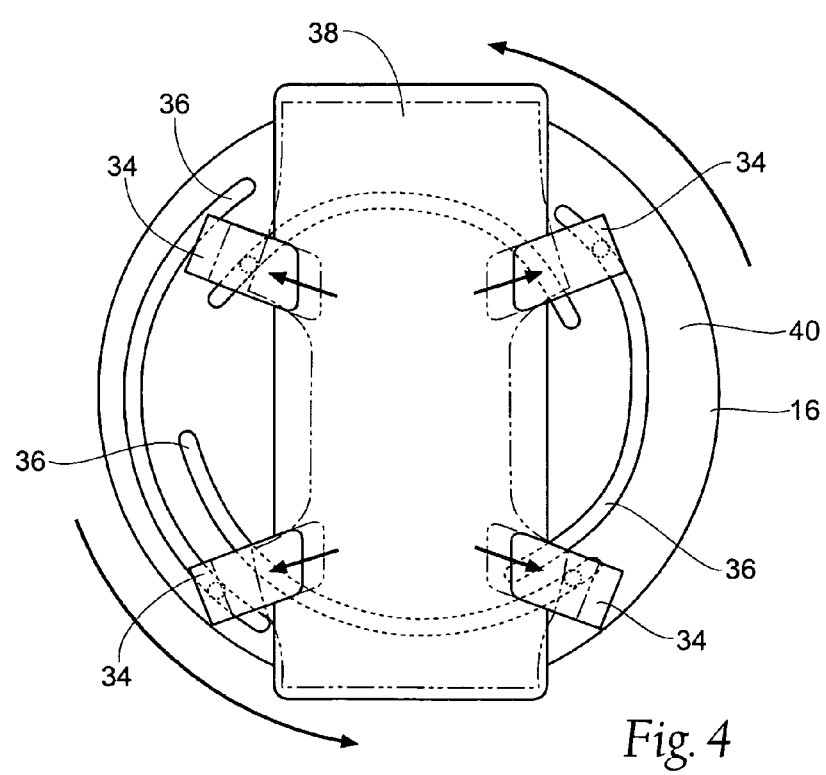
FIG. 4 is a top view of an embodiment of an active pad turning puck of the present invention.

In use, rotation of the puck assembly 38 relative to a cam plate 40 causes cam followers 32 to track through channels 36. Channels 36 are of an increasing radius from the center of the cam plate 40. Because cam followers 32 are coupled with vacuum slides 34, rotation of the puck assembly 38 relative to the cam plate 40 causes sliding of the vacuum slides inwardly and outwardly as shown in FIG. 4. The cam followers 32 are urged inwardly and outwardly due to the increasing radius of the channels 36 in a first direction of travel, and the decreasing radius of channels 36 in the second rotational direction of travel, preferably in a washing machine-like back and forth style.

Figure 5:
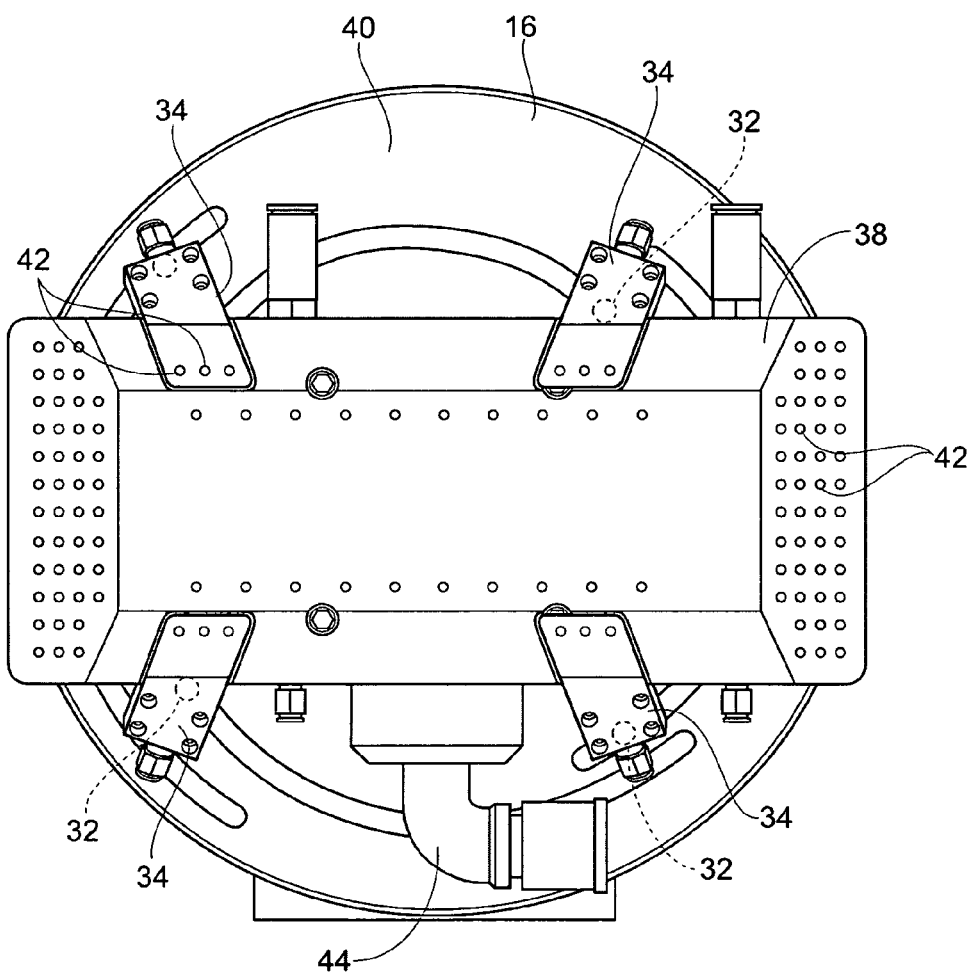
FIG. 5 is a top view of an embodiment of an active pad turning puck of the present invention.

Referring now to FIG. 5, a top view the active pad turning puck 16 of the present invention is shown. In this embodiment, vacuum ports 42 are shown, and may be applied to the vacuum slides 34, the puck assembly 38, or both. The vacuum ports are coupled to a manifold 44 and ultimately a source of vacuum (not shown).

Figure 6:
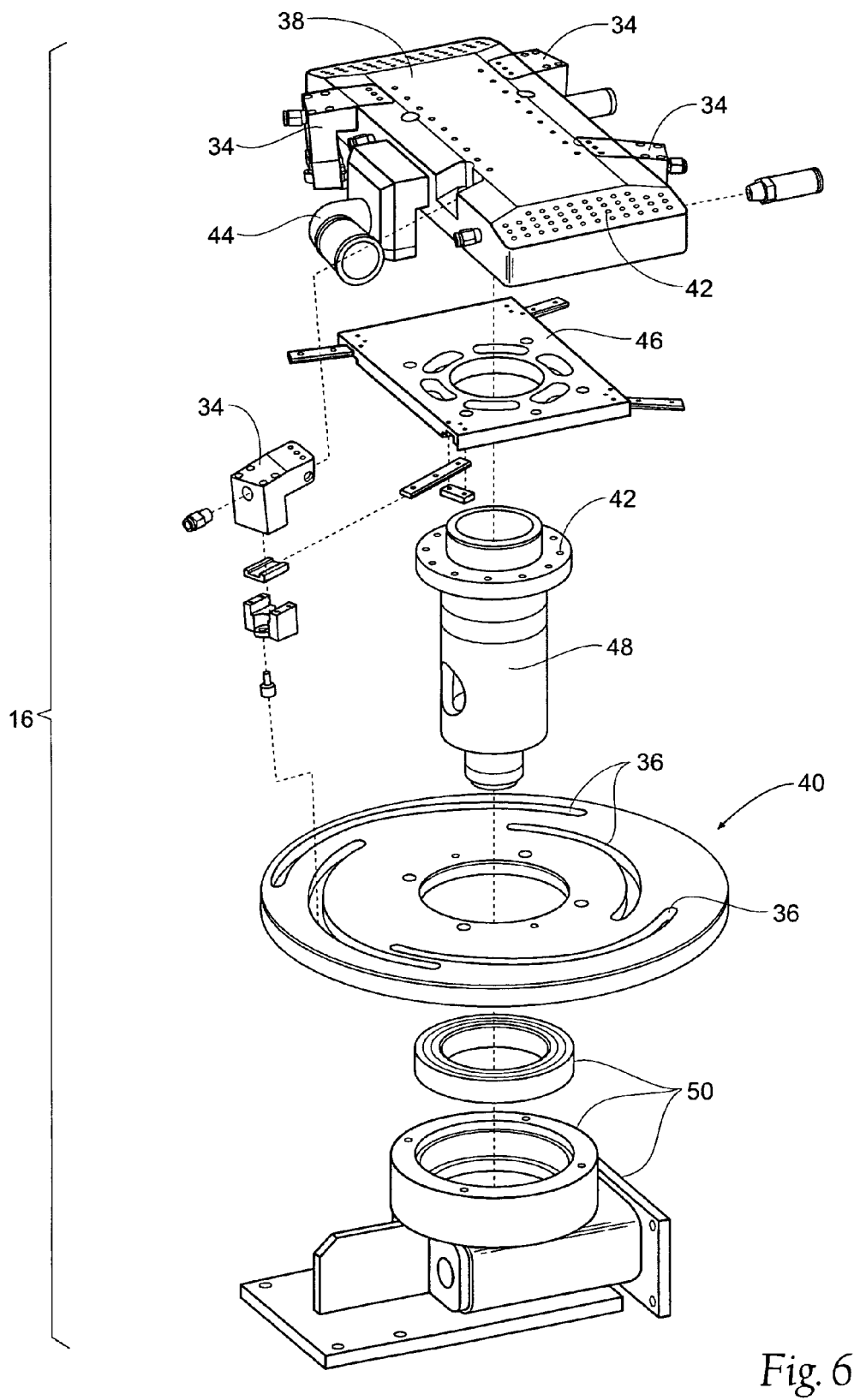
FIG. 6 is an exploded view of an active pad turning puck of the present invention.

Referring now to FIG. 6, an exploded view of the active pad turning puck 16 of the present invention is shown. In this embodiment, a shaft adaptor plate 46 is shown to receive shaft 48, through a void provided proximal to the center of cam plate 40. The support subassembly 50 is provided for coupling of the puck 16 to the pad turning device 12.

Figure 7:
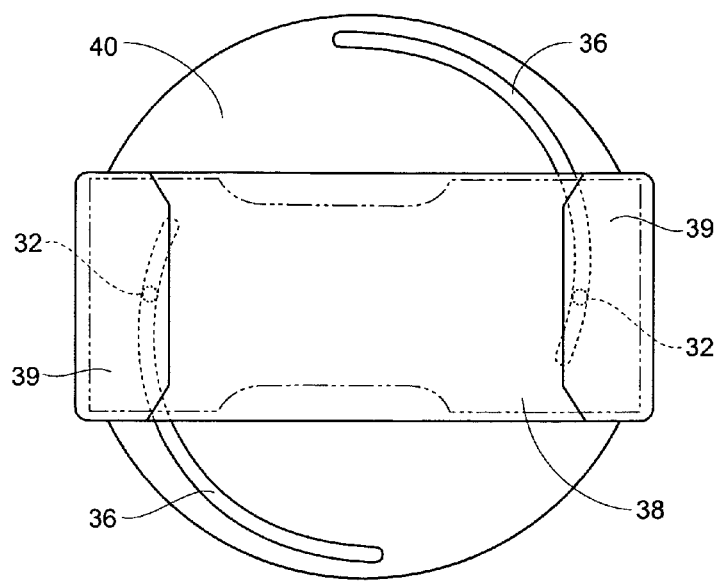
FIG. 7 is a top view of an alternate embodiment of an active pad turning puck of the present invention.
Figure 8:
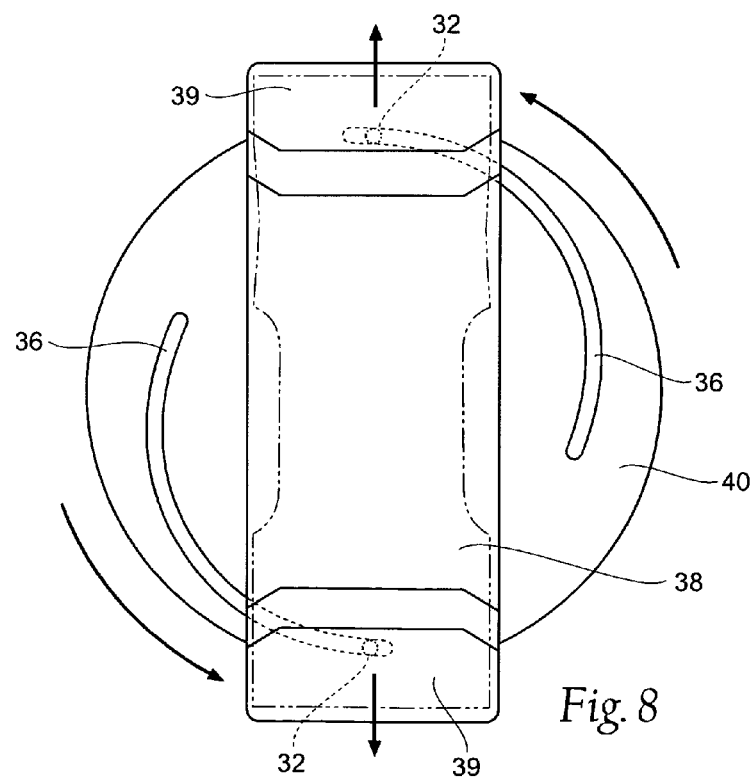
FIG. 8 is a top view of an alternate embodiment of an active pad turning puck of the present invention.

Referring now to FIG. 7, a top view of an alternate embodiment of an active pad turning puck 16 of the present invention is shown. In this embodiment, ends 39 of the puck assembly 38 are slidably enabled, as the vacuum slides 34 described previously. Rotation is again a driving force of sliding movement caused by the cam follower 32 coupled to the ends 39, as shown in FIG. 8.

Figure 9:
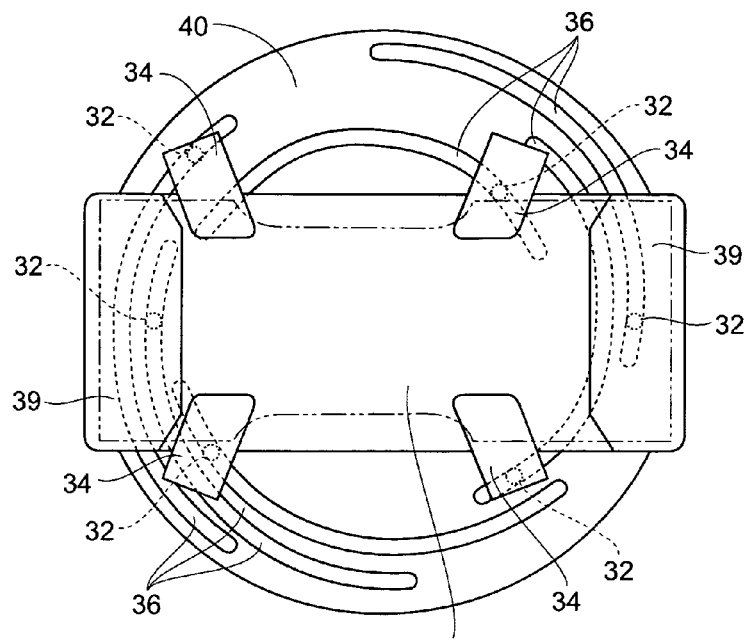
FIG. 9 is a top view of an additional alternate embodiment of an active pad turning puck of the present invention.
Figure 10:
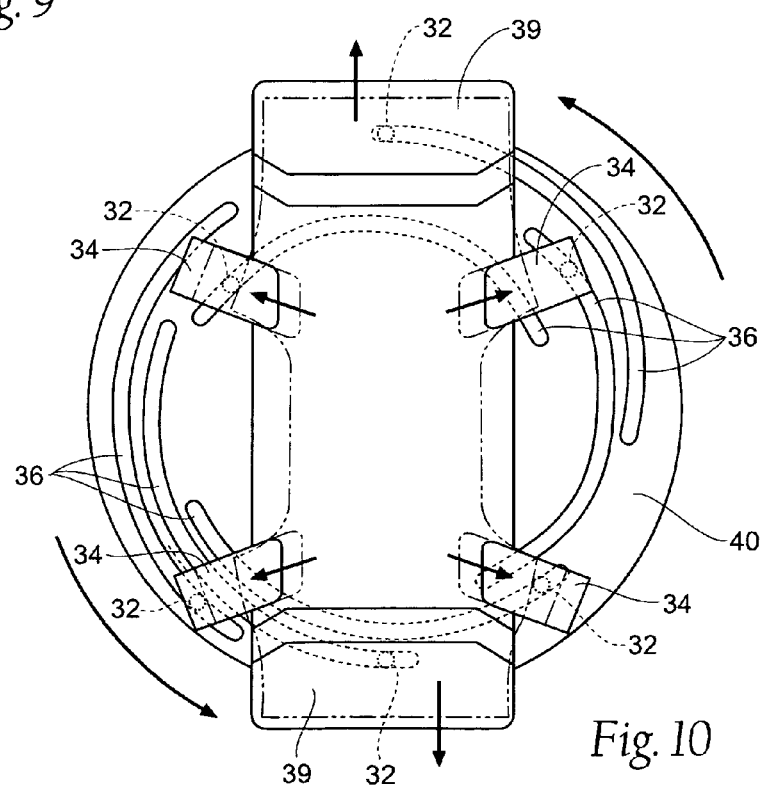
FIG. 10 is a top view of an additional alternate embodiment of an active pad turning puck of the present invention.

Referring now to FIGS. 9 and 10, a top view of an additional alternate embodiment of an active pad turning puck 16 of the present invention is shown. In this embodiment, a plurality of channels 36 are provided, each channel 36 receiving a cam follower 32 coupled to a slidable element, either ends 39 or slides 34. Of course, a single circuitous channel 36 could be provided for receiving multiple cam followers 32. Again, cam followers 32, upon rotation, urge the slidable elements outward and inward.

Figure 11:
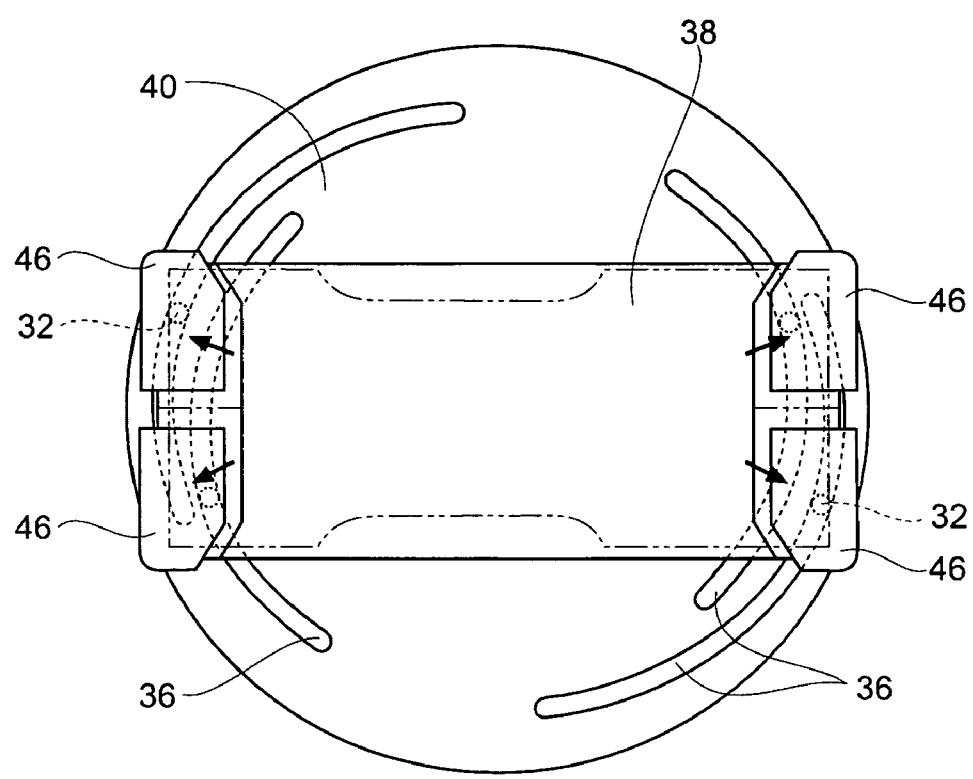
FIG. 11 is a top view of an additional alternate embodiment of an active pad turning puck of the present invention.

Referring now to FIG. 11, an additional alternative embodiment of a puck 16 of the present invention is shown. In this embodiment, it can be seen that a slidable elements 46 are provided at corners of the puck assembly 38. These slidable elements 46 will move somewhat radially away from the center of the puck 16, although the direction of movement can be controlled through different arrangements of the channel or channels 36.

In use, the transfer apparatus 10 rotates from the pick up point, stretches the article 14 while the article is upon a puck 16 by slidable elements, and deposits the article 14 on a conveyor 28 or the like for downstream processing. As the puck 16 rotates between the pick up and deposition points, the cam followers are urged into an increasing radius of the channel 36. Between the deposition point and the next subsequent pick up point, the puck 16 will rotate back to its initial position, and the cam followers are urged into an its decreasing radius of the channel 36, causing the slidable elements 34 or 39 to return to their initial, retracted position, ready to receive another article 14.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method for transferring articles from a first conveying device onto a second conveying device comprising:
   providing a plurality of rotating bodies, said rotating bodies rotating about a common axis to carry said articles rotationally in a machine direction from an upstream conveyor to a downstream lay down point, said machine direction comprising a general direction movement of said articles from a start of a web converting process to a finish of said web converting process;
   said rotating bodies having first, second and third article carrying surfaces not sharing a common plane;
   acquiring said articles from said upstream conveyor with said rotating bodies;
   while said rotating bodies are carrying said articles in a machine direction, rotating said rotating bodies in a cross-machine direction to re-orient said articles, said cross-machine direction comprising a direction generally perpendicular to said machine direction;
   while said rotating bodies are carrying said articles in a machine direction, sliding said first and said third article carrying surfaces;
   depositing said re-oriented articles at a lay down point.

* * * * *